(12) United States Patent
Horn et al.

(10) Patent No.: US 10,028,508 B2
(45) Date of Patent: Jul. 24, 2018

(54) USE OF ACTIVE COMPOUND COMPOSITIONS

(71) Applicant: BAYER CROPSCIENCE AKTIENGESELLSCHAFT, Monheim am Rhein (DE)

(72) Inventors: Karin Horn, Düsseldorf (DE); Rainer Sonneck, Leverkusen (DE); Arnoldus Vermeer, Monheim (DE); Sebastian Horstmann, Leverkusen (DE); Guenther Nentwig, Leverkusen (DE); Frederic Schmitt, Saint Didier de Formans (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/320,192

(22) PCT Filed: Jun. 19, 2015

(86) PCT No.: PCT/EP2015/063798
§ 371 (c)(1),
(2) Date: Dec. 19, 2016

(87) PCT Pub. No.: WO2015/197482
PCT Pub. Date: Dec. 30, 2015

(65) Prior Publication Data
US 2017/0150722 A1   Jun. 1, 2017

(30) Foreign Application Priority Data

Jun. 24, 2014 (EP) ..................... 14173656

(51) Int. Cl.
| | | |
|---|---|---|
| *A01N 43/78* | (2006.01) | |
| *A01N 37/02* | (2006.01) | |
| *A01N 53/00* | (2006.01) | |
| *A01N 47/40* | (2006.01) | |

(52) U.S. Cl.
CPC ............. *A01N 53/00* (2013.01); *A01N 47/40* (2013.01)

(58) Field of Classification Search
CPC ............................. C07D 277/24; A01N 37/02
USPC ................................................... 514/365, 546
See application file for complete search history.

(56) References Cited

FOREIGN PATENT DOCUMENTS

| WO | 02/30200 A1 | 4/2002 |
|---|---|---|
| WO | 2005/070210 A1 | 8/2005 |
| WO | 2013/117521 A1 | 8/2013 |

OTHER PUBLICATIONS

International Search Report of International Patent Application No. PCT/EP2015/063798 dated Aug. 28, 2015.

*Primary Examiner* — Raymond J Henley, III
(74) *Attorney, Agent, or Firm* — McBee Moore Woodward & Vanik IP, LLC

(57) ABSTRACT

The invention is in the technical field of vector control as well as insecticide-resistant mosquito and bed bug control. The active compound compositions of this invention are used against mosquitos and bed bugs which transmit disease pathogens or which annoy the well-being of humans and animals. The active compound compositions of this invention are in particular useful to overcome target-specific and/or metabolic-specific resistance of mosquitos and bed bugs and are biologically efficient on a variety of surfaces over an extended period of time.

20 Claims, No Drawings

USE OF ACTIVE COMPOUND COMPOSITIONS

CROSS-REFERENCE TO RELATED APPLICATIONS

This application is a National Stage entry of International Application No. PCT/EP2015/063798, filed Jun. 19, 2015, which claims priority to European Patent Application No. 14173656.1, filed Jun. 24, 2014.

BACKGROUND

Field

The invention is in the technical field of vector control as well as insecticide-resistant mosquito and bed bug control. The active compound compositions of this invention are used against mosquitos and bed bugs which transmit disease pathogens or which annoy the well-being of humans and animals. The active compound compositions of this invention are in particular useful to overcome insecticide-resistance of mosquitos and bed bugs and are biologically efficient on a variety of surfaces over an extended period of time.

The present invention relates to new use of active compound compositions which have very good insecticidal and arachnidial properties and which comprise firstly the known active synthethic pyrethroid compound deltamethrin and secondly at least one further known insecticidal active compound selected from the group of neonicotinoids.

Description of Related Art

It is known that the pyrethroid deltamethrin can be employed for controlling animal pests, in particular insects. It has been also disclosed that neonicotinoids such as acetamiprid, clothianidin, dinotefuran, imidacloprid, nitenpyram, thiacloprid and thiamethoxam can be used for controlling unwanted pests. Deltamethrin and neonicotinoids are known and described e.g. in "The Pesticide Manual", 16th Edition, British Crop Protection Council (deltamethrin, page 241; acetamiprid, page 9; clothianidin, page 225; dinotefuran, page 384; imidacloprid, page 640; nitenpyram, page 809; thiacloprid, page 1102; thiamethoxam, page 854). WO2002/030202A2 relates to a method of preventing damage to the seed and/or shoots and foliage of a plant by a pest which includes treating the seed from which the plant grows with a composition that includes a combination of clothianidin and at least one pyrethrin or synthetic pyrethroid. WO2002/030202A2 does not disclose the use of the combination of neonicotinoids such as clothianidin with deltamethrin for vector control uses in particular against insecticide-resistant pests.

WO2004/064522 relates to the use of an arthropod-repelling constituent of the pyrethroid/pyrethrin class combined with an agonist of the nicotine-producing acetylcholine receptors of arthropods, for efficiently repelling arthropods, preferably on animals (for animal health purposes), for a long time. WO2002/030202A2 does not disclose the use of the combination of neonicotinoids such as clothianidin with deltamethrin for vector control uses in particular against insecticide-resistant pests.

Frédéric Darriet et al., Pest Manag Sci, 2013, 69:905-910 discloses in table 3 combinations of deltamethrin with piperonyl butoxid (PBO) and various neonicotinoids such as thiamethoxam, nitenpyram, thiacloprid, imidacloprid, clothianidin and acetamiprid. PBO is known as an insecticide synergist that—despite having no insecticidal activity on its own—enhances the potency of certain pesticides such as e.g. pyrethroids (see e.g. table 2; results achieved with the combination of deltamethrin and PBO e.g. the $P^a$ value). As the combination of deltamethrin with PBO is already synergistic it is of no surprise that the addition of a neonicotinoid also leads to synergism (see table 3). However, this publication does not teach that a skilled person in the art can also achieve synergism against resistant strains of *Aedes aegypti* with the combination of deltamethrin and a neonicotinoid without PBO.

WO2005/070210A1 relates to an insecticidal composition comprising a pyrethroid and a second insecticide selected from the group of imidacloprid, nithiazine, thiamethoxam, dinotefuran, nitenpyram, thiacloprid, clothianidin and chlorfenapyr, with significantly improved knock down and mortality characteristics when applied to general household pests. WO2005/070210A1 does not disclose that the subject matter of the present invention. In particular, WO2005/070210A1 does not disclose the use of the combination of deltamethrin and a neonicotinoid for vector control. Furthermore, WO2005/07021A1 does not disclose the use of the claimed combination for insecticide-resistant mosquito and/or insecticide resistant bed bug control.

Pyrethroids are the only insecticides that have obtained WHO recommendation against Malaria vectors for both Indoor Residuals Sprays (IRS) and Long Lasting Insecticidal Mosquito Nets (LLINs), in the form of alpha-cypermethrin, bifenthrin, cyfluthrin, permethrin, deltamethrin, lambda-cyhalothrin and etofenprox. It has been the chemical class of choice in agriculture and public health applications over the last several decades because of its relatively low toxicity to humans, rapid knock-down effect, relative longevity (duration of 3-6 months when used as IRS), and low cost. However, massive use of pyrethroids in agricultural applications and for vector control led to the development of resistance in major Malaria and Dengue vectors. Strong resistance has e.g. been reported for the pyrethroid deltamethrin (and permethrin) for the *Anopheles gambiae* Tiassalé (from southern Côte d'Ivoire) strain (Constant V. A. Edi et al., Emerging Infectious Diseases; Vol. 18, No. 9, September 2012). Pyrethroid resistance was also reported for permethrin, deltamethrin and lambda-cyhalothrin for the *Aedes aegypti* Cayman Island strain (Angela F. Harris et al., Am. J. Trop. Med. Hyg., 83(2), 2010) and alpha-cypermethrin, permethrin and lambda-cyhalothrin for certain *Anopheles* strains (Win Van Bortel, Malaria Journal, 2008, 7:102).

Bed bug control has (again) become a major task as a resurgence of bed bug infestations has occurred over the last 10 years. In this connection, it has also been reported that these insects have developed resistance to pyrethroids such as deltamethrin and beta-cyfluthrin (Zach N. Adelman et al, PloS ONE, October 2011, Vol 6, Issue 10).

SUMMARY

Due to the emerging resistance in mosquitoes and bed bugs against certain pyrethroids there is an ongoing need for alternative solutions and strategies in particular for vector and bed bug control management. It is a further objective to avoid the use of piperonyl butoxid (PBO; while achieving similar/better synergistic effects) as a formulation with PBO is more expensive, more difficult to formulate (as PBO has a complex physico-chemical profile) and in general less reliable in effect, residuality and storage stability. With the present invention it has now been surprisingly found that the active compound composition comprising deltamethrin and secondly at least one further active compound selected from the group of neonicotinoids can be used without PBO for vector control and insecticide-resistant mosquito control as well as for insecticide-resistant bed bug control.

With the present invention it has now also been found that active compound compositions comprising deltamethrin (herein referred to as active compounds of group A) and secondly at least one further active compound selected from the group of neonicotinoids (herein referred to as active compounds of group B) are synergistically active without PBO and are suitable for controlling animal pests and in particular to control insecticide-resistant animal pests. Owing to this synergism, markedly lower amounts of active compound may be used and/or an existing insecticide resistance can be overcome, that is to say the effect of the mixture exceeds the effect of the individual components. The synergism is in particular surprising in connection with the control of insecticide-resistant mosquitos and/or bed bugs. The synergism is particularly pronounced after an extended period of time (e.g. 11 weeks or more after application of the active compound composition on a surface (particularly on porous and/or alkaline surfaces) and preferably 30 and more preferably 60 weeks after application).

As a consequence the active compound composition of the invention has a long-term activity. Longer-term protection can reduce the exposure of the user, the inhabitants, the domestic animals and the environment to a minimum, because active substance needs to be applied less frequently.

DETAILED DESCRIPTION OF A PREFERRED EMBODIMENT

In a preferred embodiment the active compound composition of the invention comprises preferably as an active compound from group A deltametrin.

The term neonicotinoids according to this invention refers preferably to a compound selected from the group of acetamiprid, clothianidin, dinotefuran, imidacloprid, nitenpyram, thiacloprid and thiamethoxam.

In another preferred embodiment the active compound composition of the invention comprises preferably as an active compound from group B clothianidin.

The active compound compositions according to the invention are particularly useful for vector control. Vector control is the prevention of transmission of diseases by vector insects (such as Encephalitis, West Nile Virus, Dengue Fever, Malaria, Rift Valley Fever, Yellow Fever). Vector control methods vary considerably in their applicability, cost and sustainability of their results. In a preferred embodiment of the invention, vector control refers to Malaria and Dengue vector control. Vectors in connection with the prevention of the transmission of diseases are preferably mosquitoes. A preferred embodiment of the invention therefore relates to the use of the active compound composition of the invention to prevent the transmission of diseases by vector insects preferably by applying the active compound composition to a surface or by spraying it into the air. When the active compound composition is applied on a surface the vector insects are killed or repelled when getting into contact with the surface preferably before they bite human beings and transmit a disease. When the active compound composition is sprayed into the air the vector insects are killed or repelled when getting into direct contact with the active compound composition in the air preferably also before they are able to bite human beings and transmit a disease.

Vector control products include indoor residual spray (IRS), insecticide treated net, long lasting insecticide net, space spray and/or spatial repellents. The active compound composition according to the invention is particularly useful for indoor residual sprays. Indoor residual sprays refer to formulations that are applied on walls and roofs of houses and domestic animal shelters in order to kill adult vector mosquitoes that land and rest on these surfaces. The primary effect of such sprays is towards curtailing Malaria and Dengue transmission by reducing the life span of vector mosquitoes so that they can no longer transmit the disease from one person to another and reducing the density of the vector mosquitoes.

In another preferred embodiment of the invention the active compound composition of the invention are used to control insecticide-resistant mosquitos and/or insecticide resistant bed bugs. The term "insecticide-resistance" is the term used to describe the situation in which the mosquitos or bed bugs are no longer killed by the standard dose of insecticide (they are no longer susceptible to the insecticide) or manage to avoid coming into contact with the insecticide). See 1.2.; p. 27; "Global Plan for Insecticide Resistance Management", WHO 2012). The term vector in the context of this application refers preferably to a mosquito.

As an example, WHO recommended standard dose of deltamethrin for indoor residual treatment against mosquito vectors is 20-25 mg/m$^2$ (http://www.who.int/whopes/Insecticides_IRS_Malaria_09.pdf). WHO recommended standard dose of deltamethrin products treatment of nets for malaria vector control is 15-25 mg/m$^2$ (http://www.who.int/whopes/Insecticides_ITN_Malaria_ok3.pdf). WHO recommended standard dose for space spraying against mosquitoes are described in the publication: http://www.who.int/whopes/Insecticides_for_space_spraying_Jul_2012.pdf. WHO recommended deltamethrin doses for bed bug control are 0.3-0.5 g/l (see Pesticides and their Application, WHO 2006; WHO/CDS/NTD/WHOPES/GCDPP/2006.1).

The term "control" insecticide-resistant mosquitoes and/or bed bugs refers to the possibility to be able to kill and/or repel mosquitoes and/or bed bugs that are insecticide-resistant (in order to avoid the biting of humans and transmission of the vectors to humans).

A further embodiment of the invention relates to the use of the active compound composition according to the invention to control target-site- and/or metabolic-resistant mosquitos and/or bed bugs. Target-site resistance refers to a form of biochemical resistance which occurs when the insecticide compound no longer binds to its target, and metabolic-resistance refers to a form of biochemical resistance which occurs when levels or modified activities of esterases, oxidases, or glutathione S-transferases (GST) prevent an insecticide compound from reaching its site of action.

In another preferred embodiment the active compound compositions of the present invention are preferably used to control insecticide-resistant mosquitos wherein the insecticide-resistant mosquitos are selected from the group of *Anopheles gambiae*, preferably the strain RSPH and *Anopheles funestus*, preferably the strain FUMOZ-R. In another preferred embodiment the active compound compositions of the present invention are used to control pyrethroid and/or (preferably and) carbamate-resistant mosquitos, preferably pyrethroid and/or (preferably and) carbamate-resistant *Anopheles gambiae* and/or *Anopheles funestus* mosquitos. More preferably, the active compound compositions of the present invention are used to control pyrethroid-resistant mosquitos, preferably pyrethroid-resistant *Anopheles gambiae* and/or *Anopheles funestus* mosquitos. Another preferred embodiment of the invention relates to the active compound compositions of the present invention used to control multi-resistant mosquitos.

The invention also relates to the use of an active compound composition according to the invention to control pyrethroid-resistant bed bugs. In a preferred embodiment, the active compound composition of the invention is used to control pyrethroid-resistant bed bugs, wherein the bed bugs have a Valine to Leucine mutation (V419L) and/or a Leucine to Isoleucine mutation (L925I) in the voltage-gated sodium channel alpha-subunit gene.

As a further embodiment of the invention, the herein described uses of an active compound composition also includes methods of using the active compound composition for the same purpose.

*Anopheles gambiae*, the strain RSPH is a multi-resistant mosquito (target-site and metabolic-resistance) that is described in the reagent catalog of the Malaria Research and Reference Reagent Resource Center (www.MR4.org; MR4-number: MRA-334).

*Anopheles funestus*, strain FUMOZ-R is a metabolic-resistant strain and is described in Hunt et al., Med Vet Entomol. 2005 September; 19(3):271-5). In this article it has been reported that *Anopheles funestus*—as one of the major malaria vector mosquitos in Africa—showed resistance to pyrethroid insecticides (lambda-cyhalothrin, deltamethrin, permethrin and carbamate) in South Africa.

Certain Bed bugs are known to be resistant to pyrethroids, wherein the pyrethroid resistance can be ascribed to metabolic resistance such as increased metabolic detoxification by P450s, glutathione transferases, and esterases as well as target-site resistance due to decreased target-site sensitivity of voltage-gated sodium channels. It has been also reported that a Valine to Leucine mutation (V419L) and/or the Leucine to Isoleucine mutation (L925I) in voltage-gated sodium channel alpha-subunit gene is responsible for target-site resistance to deltamethrin in bed bugs (Fan Zhu et al., Archives of Insect Biochemistry and Physiology, 2010, Vol. 00, No 0, 1-13).

Pyrethroid and/or (preferably and) carbamate-resistant mosquitos/bed bugs are mosquitos/bed bugs that are resistant to the treatment of pyrethroid insecticides and/or (preferably and) carbamate insecticides. Pyrethroid insecticides are e.g. allethrin, bifenthrin, cyfluthrin, cypermethrin, cyphenothrin, deltamethrin, esfenvalerate, etofenprox, fenpropathrin, fenvalerate, flucythrinate, imiprothrin, lambda-cyhalothrin, metofluthrin, permethrin, prallethrin resmethrin, silafluofen, sumithrin, tau-fluvalinate, tefluthrin, tetramethrin, tralomethrin, transfluthrin. Carbamate insecticides are e.g. aldicarb, benfuracarb, carbaryl, carbofuran, carbosulfan, fenobucarb, methiocarb, methomyl, oxamyl, thiodicarb, triazamate. In a more preferred embodiment the term "Pyrethroid" in the context of "pyrethroid-resistant mosquitos/bed bugs refers to a compound selected from the group of cyfluthrin, cypermethrin, lambda-cyhalothrin, deltamethrin and permethrin. In a more preferred embodiment pyrethroid resistance exists in regard to at least one pyrethroid selected from the group of lambda-cyhalothrin, deltamethrin and permethrin.

Multi-resistant mosquitos refers to a mosquitos where several different resistance mechanisms are present simultaneously such as target-site resistance and metabolic resistance. The different resistance mechanisms may combine to provide resistance to multiple classes of products (IRAC publication: "Preventation and Management of Insecticide Resistance in Vectors of Public Health Importance"; second edition; 2011).

In a preferred embodiment, the active compound combinations according to the invention have synergistic actions preferably in regard to the above outlined uses. In a more preferred embodiment, the active compound combinations according to the invention show synergistic effects against metabolic-resistant mosquitos, preferably against *Anopheles funestus*, more preferably against the strain FUMOZ-R. The synergistic effects can be observed, for example, when commercially available formulations of active compounds of group A and group B or pure technical compounds of group A and group B are applied together. The synergism is particularly pronounced (in particular against metabolic-resistant mosquitos, preferably against *Anopheles funestus*, more preferably against the strain FUMOZ-R) after the active compound combination has been applied to a certain surface and biological activity is measured after a certain period of time (preferably 11 weeks, more preferably 30 weeks and even more preferably 60 weeks after application). This improved long-term activity/long residuality applies in particular to the treatment of porous and/or alkaline surfaces, such as concrete, render, ashlar/brick, timber (treated and untreated), ceramic, straw or thatch, chalky, limy, gypsiferous, cement-containing and loamy surfaces. Here, upon application to non-porous surfaces, the activity remains unaffected on the whole. A preferred embodiment of the present invention is therefore the use of an active compound composition according to the present invention wherein the active compound combination is applied to a surface and wherein the surface-applied active compound combination acts synergistically after a period of at least 11 weeks (preferably 30 and more preferably 60 weeks) without additional active compound composition application on the same surface. This activity ends 2 years, preferably 1.5 years, more preferably 70 weeks and most preferably 65 weeks after application of the active compound combination on the corresponding surface.

The active compound compositions according to the invention can be applied to any surface inside buildings or in the open, for example wallpaper, concrete, render, ashlar, timber (treated and untreated), ceramic (glazed and unglazed), straw or thatch, brick (untreated, limewashed, painted), clay minerals (for example terracotta), chalky, limy, gypsiferous, cement-containing and loamy surfaces.

Another embodiment refers to a use of the active compound composition according to the invention wherein the composition is applied only once to a surface for a time period of at least 11 weeks (preferably for a time period of at least 30 weeks and more preferably for 60 weeks). Therefore, the active compound composition of the invention has a residuality of at least 11 weeks (preferably at least 30 weeks and more preferably at least 60 weeks). According to the WHOPES directive "Guidelines for testing mosquito adulticides for indoor residual spraying and treatment of mosquito nets" (see http://www.who.int/whopes/guidelines/en/; see section 2.4.2.1) "residuality" is fulfilled when the mortality is higher or equals 80% after 24 hours.

The synergistic effects permit a reduction of the application rates, a higher efficacy at the same application rate and/or a reduction in the number of individual applications required and/or to overcome an existing insecticide resistance and—as a result for the user—an economically and ecologically improved resistant management of mosquitos and bed bugs.

For example, the combinations of the active compounds of group A and group B allow the activity to be synergistically enhanced in a manner which far and unexpectedly exceeds the activities which can be achieved with the formulations of the individual active compounds of group A and group B.

The ratio of the compounds of group A employed to the compounds of group B, and the total amount of the mixture to be employed, depend on the particular mosquito/bed bug strain and the occurrence of the mosquito/bed bugs. The optimal ratios and overall rates used can be determined for each application by test series.

The application rate of the active compound combinations according to the invention varies preferably within ranges of between 0.001 and 1000 mg/m$^2$, more preferably, 2 and 500 mg/m$^2$ and even more preferred between 50 and 250 mg/m$^2$.

The mixing ratio of the active compounds of deltamethrin (compound of group A) with clothianidin (compound of group B) is advantageously and preferably for the use of mosquitos from 1:1 to 1:200, preferably from, 1:1 to 1:40, more preferably from 1:2 to 1:20, even more preferably from 1:4 to 1:10, most preferably 1:8.

As a further unexpected result it has been found that the combination of deltamethrin and clothianidin is efficient against the herein discussed pests (and in particular mosquitoes, preferably metabolic-resistant mosquitos, preferably *Anopheles funestus*, more preferably the strain FUMOZ-R) on surfaces such as concrete, tile and wood.

The active compound combination according to the invention may comprise further components, for example additional active compounds of a different type (e.g. other insecticides, antibacterial compounds, fungicides, herbicides etc.) and/or additives customary in crop protection and/or formulation auxiliaries, or may be used together with these compounds. However, the active compound combination according to the invention does not comprise piperonyl butoxid (PBO).

The active compound combinations of the invention can be converted to customary formulations, such as solutions, emulsions, wettable powders, suspensions, powders, dusts, pastes, soluble powders, granules (such as water dispersible granules), suspension-emulsion concentrates, tablets, bait formulations, smoke producing formulations, gels, foams, aerosols, natural materials impregnated with the active compound combinations of the invention, synthetic materials impregnated with the active compound combinations of the invention and microencapsulations of the active compound combinations of the invention in polymeric substances. These formulations can be used directly, as "ready to use", or after dilution in the application medium.

These formulations are produced in a known manner, for example by mixing the active compounds/active compound combination with extenders, that is liquid solvents and/or solid carriers, optionally with the use of surfactants, that is emulsifiers and/or dispersants, adjuvants, that is substances which improve the biological performance without having an own biological activity, antifoam, preservatives, antioxidants, colourants, anti-freeze, pH stabilizers, thickeners, and/or foam-formers.

Suitable for use as auxiliaries are substances which are suitable for imparting to the active compounds/active compound combination itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolyzates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Thickeners such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

In a particularly preferred embodiment the active compound combinations of the invention are converted to suspensions concentrates (SC), water dispersable granules (WG) or wettable powders (WP). Suspension concentrates (SCs) are usually made by premixing the active ingredient powder in an aqueous solution of a liquid extender and a dispersant, followed by a wet grinding process in a bead mill to give a particle size in the range of 1-10 microns. Water dispersable granules (WGs) can be formulated using various processing techniques, resulting in products which redisperse or dissolve in water e.g. in the spray tank. The main processes for granulation to achieve WGs for the active compound combinations of the invention are: a) pan granulation, b) high speed mixing agglomeration, c) extrusion granulation, d) fluid bed granulation, e) fluid bed spray granulation, f) spray drying, possibly with in-built agglomeration process. Wettable powders (WPs) are usually made from solid active ingredients which are fine grinded through a hammer or pin type mill or a fluid energy micronizer. The powders contain dry surfactants as powder wetting and dispersing agents and inert carriers or fillers. WPs are preferably used in water-soluble bags. Water-soluble bags are known to a skilled person in the art and may e.g. consist of polyvinyl alcohol (PVA) or other water-soluble material.

The active compound composition of the invention can be used for liquid applications such as e.g. a spray solution to control animal pests on a variety of surfaces. The treatment of surfaces for example within or outside from buildings is necessary to control spreading of diseases that are transmitted by vectors (such as mosquitos) that transmit diseases or that annoy animals and humans. There is a great need for protecting the inhabitants effectively and with a long-lasting residuality. Moreover, reasons of hygiene and structural engineering require that animal pests be prevented from entering into buildings, spreading and dwelling in buildings and infesting wood or other materials.

Other uses include the integration or coating of the active compound composition according to the invention into/of materials such as pellets, granules, dusts, yarns, foils, sleeping mats, mosquito nets, textiles, wovens, braids, knits, felts, nonwovens, curtains, draperies, tarpaulins, fabrics, wood, papers, furnitures, fences in particular animal fences, paints etc. (integration of active ingredients into foils and mosquito nets is e.g. described in WO-A-2009/121580; PCT/EP2011/0055822, WO2011/128380).

The present invention also relates to a material which comprises the active compound composition of the invention. The material is preferably selected from the group of foil, sleeping net, sleeping mat, mosquito net, textile, woven, braid, knit, felt, nonwoven, curtain, drapery, tarpaulin, fabric, wood, paper, furniture, fence preferably animal fence, paint.

Another preferred embodiment of the invention relates to a bed bug bait which comprises the active compound composition of the invention and means to attract bed bugs. Means to attract bed bugs are known to a skilled person in the art (see e.g. WO 2011/149899).

Alternatively, in another embodiment of the invention, the active compound combination is used to control bed bugs via an ovicidial activity. For this purpose, the active compound combination of the invention is applied to (e.g. sprayed on) bed bugs and eggs directly (such as e.g. on bedsprings, box springs, and the interior of bed frames or headboards, including all cracks and joints).

A further embodiment of this invention relates to the use of the above described material to control animal pests, preferably arthropods, preferably insects and more preferably mosquitos and/or bed bugs in particular insecticide-resistant mosquitos and/or insecticide-resistant bed bugs and more preferably mosquitos and/or bed bugs that are target-site- and/or metabolic-resistant. Another preferred embodiment relates to the use of such a material to control insecticide-resistant mosquitos wherein the insecticide-resistant mosquitos are selected from the group of *Anopheles gambiae*, preferably the strain RSPH and *Anopheles funestus*, preferably the strain FUMOZ-R. In another preferred embodiment the current invention relates to the use of such a material to control pyrethroid and/or carbamate-resistant mosquitos, preferably pyrethroid and/or carbamate-resistant *Anopheles gambiae* and/or *Anopheles funestus* mosquitos. More preferably, the material of the present invention is used to control pyrethroid-resistant mosquitos, preferably pyrethroid-resistant *Anopheles gambiae* and/or *Anopheles funestus* mosquitos. Another preferred embodiment of the invention relates to the use of such a material to control multi-resistant mosquitos.

The invention also relates to the use of the above described material to control pyrethroid-resistant bed bugs. In a preferred embodiment, the material is used to control pyrethroid-resistant bed bugs, wherein the bed bugs have a Valine to Leucine mutation (V419L) and/or a Leucine to Isoleucine mutation (L925I) in the voltage-gated sodium channel alpha-subunit gene.

The good insecticidal activity of the active compound combinations is illustrated by the examples below. Whereas the individual active compounds show weaknesses in their activity, the combinations show an activity which exceeds a simple addition of activities.

A synergistic effect of the active compound combination is always present when the activity of the active compound combination exceeds the total of the activities of the active compounds when applied individually.

The expected activity for a given combination of two active compounds can be calculated according to S. R. Colby, Weeds 15 (1967), 20-22 as follows:

If

X is the kill rate, expressed in % of the untreated control, when active compound A is applied at an application rate of m g/ha or at a concentration of m ppm, Y is the kill rate, expressed in % of the untreated control, when active compound B is applied at an application rate of n g/ha or at a concentration of n ppm and E is the kill rate, expressed in % of the untreated control, when active compounds A and B are applied at application rates of m and n g/ha or at a concentration of m and n ppm, then $$E = X + Y - \frac{X \cdot Y}{100}$$

If the actual insecticidal kill rate is greater than calculated, the kill of the combination is superadditive, i.e. there is a synergistic effect. In this case, the actual observed kill rate has to be greater than the value for the expected kill rate (E or hereinafter in the tables also Colby exp. %) calculated from the formula given above.

If, in the context of this description, the short form of the "common name" of an active compound is used, this comprises in each case all customary derivatives, such as the esters and salts, and isomers, in particular optical isomers, especially the commercially available form or forms. If the "common name" refers to an ester or a salt, this in each case also comprises all other customary derivatives, such as other esters and salts, the free acids and neutral compounds, and isomers, in particular optical isomers, especially the commercially available form or forms. The terms "combination" and "composition" are used as synonyms throughout this application.

Examples

1. Metabolic-Resistant *Anopheles* Test
Solvent: Acetone

To produce a suitable preparation of active compound combination the active compounds deltamethrin and clothanidin were dissolved in acetone (for the control group only one active compound was dissolved in acetone). The active compound combination preparation (and the active compound preparations) were pipetted onto a glazed tile, wood and concrete and, after drying, adult mosquitoes of the species *Anopheles funestus* metabolic-resistant strain FUMOZ-R (Hunt et al., Med Vet Entomol. 2005 September; 19(3):271-5) are placed onto the treated tile, wood and concrete. The exposition time is 30 minutes.

1 hour, 2 hour, 4 hour, 24 hours after contact to the treated surface, the mortality proportion of the test animals in % is determined. Here, 100% means that all mosquitoes have been killed; 0% means that none of the mosquitoes has been killed. The treated tile, wood and concrete was stored under stress conditions (30° C./80% rh). Measurement with the treated tile, wood and concrete was repeated 5 weeks (Table 1), 11 weeks (Table 2) and 60 weeks (Table 3) after the treatment with the active compound combination.

TABLE 1

Deltamethrin and Clothianidin/*Anopheles funestus*/Mortality 5 weeks after treatment

| | Concentration/ mg/m2 Deltamethrin | Concentration/ mg/m2 Clothianidin | | 1 h | 2 h | 4 h | 24 h | 1 h | 2 h | 4 h | 24 h | 1 h | 2 h | 4 h | 24 h |
|---|---|---|---|---|---|---|---|---|---|---|---|---|---|---|---|
| | | | | \multicolumn{12}{c}{Surface} |
| | | | | \multicolumn{4}{c}{Tile} | \multicolumn{4}{c}{Wood} | \multicolumn{4}{c}{Concrete} |
| Deltamethrin | 12.5 | 0 | Effect % | 17 | 77 | 97 | 100 | 10 | 77 | 80 | 77 | 70 | 87 | 100 | 30 |
| alone | 25 | 0 | Effect % | 7 | 83 | 100 | 93 | 30 | 90 | 93 | 83 | 90 | 100 | 100 | 73 |
| Clothianidin | 0 | 100 | Effect % | 0 | 7 | 7 | 80 | 7 | 20 | 27 | 93 | 15 | 10 | 30 | 93 |
| alone | 0 | 200 | Effect % | 0 | 0 | 10 | 90 | 7 | 10 | 20 | 93 | 3 | 17 | 30 | 83 |
| Deltamethrin | 12.5 | 100 | Effect % | 20 | 60 | 97 | 80 | 50 | 77 | 93 | 83 | 67 | 100 | 100 | 93 |
| and | 12.5 | 100 | Colby exp. | 17 | 78.61 | 97.2 | 100 | 16.3 | 81.6 | 85.4 | 98.39 | 74.5 | 88.3 | 100 | 95.1 |
| Clothianidin | 25 | 100 | Effect % | 43 | 80 | 83 | 80 | 30 | 83 | 93 | 87 | 80 | 95 | 100 | 97 |
| | 25 | 100 | Colby exp. | 7 | 84.19 | 100 | 98.6 | 34.9 | 92 | 94.9 | 98.81 | 91.5 | 100 | 100 | 98.1 |
| | 12.5 | 200 | Effect % | 17 | 90 | 100 | 77 | 3 | 60 | 87 | 97 | 70 | 90 | 100 | 97 |
| | 12.5 | 200 | Colby exp. | 17 | 77 | 97.3 | 100 | 16.3 | 79.3 | 84 | 98.39 | 70.9 | 89.2 | 100 | 88.1 |
| | 25 | 200 | Effect % | 60 | 97 | 100 | 97 | 73 | 100 | 100 | 100 | 75 | 95 | 100 | 93 |
| | 25 | 200 | Colby exp. | 7 | 81 | 100 | 99.3 | 34.9 | 91 | 94.4 | 98.81 | 90.3 | 100 | 100 | 95.4 |

TABLE 2

Deltamethrin and Clothianidin/*Anopheles funestus*/Mortality 11 weeks after treatment

| | Concentration/ mg/m2 Deltamethrin | Concentration/ mg/m2 Clothianidin | | 1 h | 2 h | 4 h | 24 h | 1 h | 2 h | 4 h | 24 h | 1 h | 2 h | 4 h | 24 h |
|---|---|---|---|---|---|---|---|---|---|---|---|---|---|---|---|
| | | | | \multicolumn{12}{c}{Surface} |
| | | | | \multicolumn{4}{c}{Tile} | \multicolumn{4}{c}{Wood} | \multicolumn{4}{c}{Concrete} |
| Deltamethrin | 12.5 | 0 | Effect % | 0 | 0 | 0 | 3 | 0 | 0 | 20 | 13 | 3 | 0 | 17 | 30 |
| alone | 25 | 0 | Effect % | 10 | 33 | 43 | 63 | 0 | 27 | 80 | 70 | 13 | 43 | 63 | 73 |
| Clothianidin | 0 | 100 | Effect % | 7 | 10 | 13 | 37 | 0 | 3 | 33 | 27 | 23 | 67 | 73 | 93 |
| alone | 0 | 200 | Effect % | 7 | 20 | 43 | 73 | 13 | 17 | 17 | 40 | 3 | 17 | 47 | 83 |
| Deltamethrin | 12.5 | 100 | Effect % | 13 | 37 | 40 | 30 | 10 | 43 | 50 | 50 | 67 | 83 | 93 | 93 |
| and | 12.5 | 100 | Colby exp. | 7 | 10 | 13 | 38.9 | 0 | 3 | 46.4 | 36.49 | 25.3 | 67 | 77.6 | 95.1 |
| Clothianidin | 25 | 100 | Effect % | 13 | 47 | 80 | 87 | 30 | 57 | 97 | 87 | 33 | 77 | 90 | 97 |
| | 25 | 100 | Colby exp. | 16.3 | 39.7 | 50.4 | 76.7 | 0 | 29.2 | 86.6 | 78.1 | 33 | 81.2 | 90 | 98.1 |
| | 12.5 | 200 | Effect % | 7 | 50 | 80 | 83 | 0 | 30 | 70 | 53 | 37 | 70 | 90 | 97 |
| | 12.5 | 200 | Colby exp. | 7 | 20 | 43 | 73.8 | 13 | 17 | 33.6 | 47.8 | 5.91 | 17 | 56 | 88.1 |
| | 25 | 200 | Effect % | 13 | 67 | 93 | 100 | 33 | 73 | 90 | 90 | 37 | 93 | 93 | 93 |
| | 25 | 200 | Colby exp. | 16.3 | 46.4 | 67.5 | 90 | 13 | 39.4 | 83.4 | 82 | 15.6 | 52.7 | 80.4 | 95.4 |

TABLE 3

Deltamethrin and Clothianidin/*Anopheles funestus*/Mortality 60 weeks after treatment

| | Concentration/ mg/m2 | Concentration/ mg/m2 | | Hours after contract to the treated surface | | | | | | | | | | | |
|---|---|---|---|---|---|---|---|---|---|---|---|---|---|---|---|
| | | | | 1 h | 2 h | 4 h | 24 h | 1 h | 2 h | 4 h | 24 h | 1 h | 2 h | 4 h | 24 h |
| | | | | | | | | | Surface | | | | | | |
| | Deltamethrin | Clothianidin | | Tile | | | | Wood | | | | Concrete | | | |
| Deltamethrin alone | 12.5 | 0 | Effect % | 0 | 0 | 17 | 30 | 0 | 0 | 17 | 43 | 0 | 0 | 0 | 13 |
| | 25 | 0 | Effect % | 0 | 7 | 23 | 53 | 0 | 10 | 37 | 43 | 0 | 0 | 0 | 23 |
| Clothianidin alone | 0 | 100 | Effect % | 0 | 0 | 0 | 17 | 0 | 0 | 0 | 10 | 0 | 3 | 20 | 37 |
| | 0 | 200 | Effect % | 0 | 3 | 7 | 43 | 0 | 3 | 3 | 17 | 0 | 7 | 17 | 63 |
| Deltamethrin and Clothianidin | 12.5 | 100 | Effect % | 0 | 7 | 17 | 40 | 0 | 23 | 53 | 60 | 0 | 13 | 23 | 77 |
| | 12.5 | 100 | Colby exp. | 0 | 0 | 17 | 41.9 | 0 | 0 | 17 | 48.7 | 0 | 3 | 20 | 45.2 |
| | 25 | 100 | Effect % | 0 | 23 | 67 | 87 | 0 | 67 | 87 | 93 | 0 | 7 | 33 | 70 |
| | 25 | 100 | Colby exp. | 0 | 7 | 23 | 61 | 0 | 10 | 37 | 48.7 | 0 | 3 | 20 | 51.5 |
| | 12.5 | 200 | Effect % | 0 | 10 | 30 | 53 | 0 | 27 | 63 | 73 | 0 | 7 | 20 | 80 |
| | 12.5 | 200 | Colby exp. | 0 | 3 | 22.8 | 60.1 | 0 | 3 | 19.5 | 52.69 | 0 | 7 | 17 | 67.8 |
| | 25 | 200 | Effect % | 0 | 0 | 67 | 73 | 0 | 13 | 43 | 63 | 0 | 13 | 60 | 83 |
| | 25 | 200 | Colby exp. | 0 | 9.79 | 28.4 | 73.2 | 0 | 12.7 | 38.9 | 52.69 | 0 | 7 | 17 | 71.5 |

2. Efficiency of Deltamethrin and Clothianidin Against Bed Bugs (*Cimex Lectularius*, Strain Cincinnati (CIN-1))

To produce a suitable preparation Deltamethrin and Clothianidin was dissolved in acetone in various concentrations. Efficacy tests were done by placing 10 bed bug test animals (*Cimex Lectularius*, strain Cincinnati (CIN-1)) onto a glazed tile and plywood. The prepared solutions in concentration of 6.25 mg/m$^2$ Deltamethrin and 50 mg/m$^2$ Clothianidin were sprayed with a glass nozzle on glazed tile and plywood. The bed bugs were added to the sprayed glazed tile and plywood 1 and 3 weeks after spraying. After 30 min. exposure time the bedbugs were transferred from the treated surface to plastic cups and the knock-down proportion of the test animals was determined 1 hour and 24 hours after the contact. Knock-down values of between 93 to 100% were measured.

The invention claimed is:

1. An active compound composition for vector control comprising deltamethrin and secondly at least one further active compound selected from the group of neonicotinoids with the proviso that the active compound composition does not comprise piperonyl butoxide, wherein the ratio of deltamethrin to said further active compound is from 1:4 to 1:16.

2. A method for vector control comprising applying an active compound composition of claim 1 where vector control is desired.

3. The method according to claim 2 for Malaria and Dengue vector control.

4. The method according to claim 2 wherein the vectors are mosquitos.

5. The method according to claim 2 wherein the vectors are insecticide-resistance mosquitos.

6. The method according to claim 5 wherein the insecticide-resistant mosquitos are target-site- and/or metabolic-resistant mosquitos.

7. The method according to claim 6 wherein the target-site- and/or metabolic-resistant mosquitos are pyrethroid and/or carbamate-resistant mosquitos.

8. The method according to claim 6 wherein the vectors are multi-resistant mosquitos.

9. The method according to claim 5 wherein the insecticide-resistant mosquitos are metabolic-resistant mosquitos selected from the group of *Anopheles funestus*, optionally the strain FUMOZ-R.

10. The method of claim 2 for target-site- and/or metabolic-resistant bed bug control.

11. The method according to claim 10 wherein the bed bugs are pyrethroid-resistant bed bugs.

12. The method according to claim 2 wherein the active compound combination is applied only once to a surface for a time period of at least 11 weeks.

13. The method according to claim 12 wherein the applied active compound combination on the surface acts synergistically after a period of at least 11 weeks without additional active compound composition application on the same surface.

14. The method according to claim 13 wherein the surface is porous and/or alkaline.

15. The active compound composition according to claim 1 wherein said further active compound comprises clothianidin.

16. The composition of claim 15 which is synergistic.

17. An active compound composition for insecticide-resistant mosquito and/or insecticide resistant bed bug control comprising deltamethrin and secondly at least one further active compound selected from the group of neonicotinoids with the proviso that the active compound composition does not comprise piperonyl butoxide wherein the ratio of deltamethrin to said further active compound is from 1:4 to 1:16.

18. An indoor residual spray comprising a synergistic combination of deltamethrin and clothianidin, wherein the ratio of deltamethrin to clothianidin is from 1:4 to 1:16, with the proviso that the spray does not comprise piperonyl butoxide.

19. A spray of claim 18, wherein said spray becomes more synergistic after 11 weeks or more after application thereof on a surface.

20. An indoor residual spray of claim 18, wherein said ratio is from 1:4 to 1:10.

* * * * *